United States Patent
O'Connell et al.

(10) Patent No.: US 9,877,660 B2
(45) Date of Patent: Jan. 30, 2018

(54) SYSTEMS AND METHODS FOR DETERMINING FRACTIONAL FLOW RESERVE WITHOUT ADENOSINE OR OTHER PHARMALOGICAL AGENT

(71) Applicant: Medtronic Vascular Galway, Ballybrit, Galway (IE)

(72) Inventors: Barry O'Connell, Ballybrit (IE); Colm Connolly, Ballybrit (IE); H. Allan Steingisser, Windsor, CA (US)

(73) Assignee: Medtronic Vascular Galway, Galway (IE)

( * ) Notice: Subject to any disclaimer, the term of this patent is extended or adjusted under 35 U.S.C. 154(b) by 861 days.

(21) Appl. No.: 14/080,433

(22) Filed: Nov. 14, 2013

(65) Prior Publication Data
US 2015/0133799 A1 May 14, 2015

(51) Int. Cl.
*A61B 5/0215* (2006.01)
*A61B 5/02* (2006.01)

(52) U.S. Cl.
CPC ........ *A61B 5/0215* (2013.01); *A61B 5/02158* (2013.01); *A61B 5/02007* (2013.01); *A61B 2562/0247* (2013.01)

(58) Field of Classification Search
None
See application file for complete search history.

(56) References Cited

U.S. PATENT DOCUMENTS 4,718,425 A   1/1988 Tanaka et al.
4,771,782 A   9/1988 Millar
(Continued)

FOREIGN PATENT DOCUMENTS

DE   102008045878   3/2010
EP        0263190   10/1986
(Continued)

OTHER PUBLICATIONS

Endoh, Kazuo, et al. "Mechanism of gastric hyperemia induced by intragastric hypertonic saline in rats." Gastroenterology—Baltimore Then Philadelphia—104 (1993): 114-114.*
(Continued)

*Primary Examiner* — Jacqueline Cheng
*Assistant Examiner* — Jairo Portilllo

(57) ABSTRACT

Embodiments hereof relate to methods and systems for determining a pressure gradient across a lesion of a vessel without requiring the use of a pharmacological hyperemic agent. A measurement system includes at least an injection catheter and a pressure-sensing instrument or guidewire slidingly disposed through the catheter, the pressure-sensing guidewire including at least one pressure sensor configured to obtain a pressure measurement for use in determining the pressure gradient across the lesion. The catheter is configured to deliver or inject a non-pharmacological fluid, such as saline or blood, across the lesion in order to increase a flow rate there-through, thereby simulating hyperemia without the use of a pharmacological hyperemic agent. Once an increased flow rate that simulates hyperemia is achieved, the pressure sensor of the pressure-sensing guidewire may be utilized to measure the pressure gradient across the lesion in order to assess the severity of the lesion.

17 Claims, 4 Drawing Sheets

(56) References Cited

U.S. PATENT DOCUMENTS

| | | |
|---|---|---|
| 4,796,641 A | 1/1989 | Mills |
| 4,815,472 A | 3/1989 | Wise |
| 4,850,358 A | 7/1989 | Millar |
| 4,901,731 A | 2/1990 | Millar |
| 4,924,877 A | 5/1990 | Brooks |
| 4,928,693 A | 5/1990 | Goodin |
| 4,936,310 A | 6/1990 | Engstrom et al. |
| 4,941,473 A | 7/1990 | Tenerz et al. |
| 4,966,148 A | 10/1990 | Millar |
| 4,966,156 A | 10/1990 | Perry et al. |
| 5,029,585 A * | 7/1991 | Lieber ............ A61B 5/0215 29/854 |
| 5,046,497 A | 9/1991 | Millar |
| 5,050,297 A | 9/1991 | Metzger |
| 5,085,223 A | 2/1992 | Lars et al. |
| 5,125,058 A | 6/1992 | Tenerz et al. |
| 5,195,375 A | 3/1993 | Tenerz et al. |
| 5,267,958 A | 12/1993 | Buchbinder et al. |
| 5,280,786 A | 1/1994 | Wlodarczyk et al. |
| 5,427,114 A | 6/1995 | Colliver et al. |
| 5,451,233 A | 9/1995 | Yock |
| 5,466,222 A | 11/1995 | Ressemann et al. |
| 5,526,820 A | 6/1996 | Khoury |
| 5,542,434 A | 8/1996 | Imran et al. |
| 5,564,425 A | 10/1996 | Tonokura |
| 5,569,219 A | 10/1996 | Hakki et al. |
| 5,573,007 A | 11/1996 | Bobo, Sr. |
| 5,591,129 A | 1/1997 | Shoup et al. |
| 5,637,091 A | 6/1997 | Hakky et al. |
| RE35,648 E | 11/1997 | Tenerz et al. |
| 5,694,946 A | 12/1997 | Tenerz et al. |
| 5,701,905 A | 12/1997 | Esch |
| 5,715,827 A | 2/1998 | Cori et al. |
| 5,813,997 A | 9/1998 | Imran et al. |
| 5,827,243 A | 10/1998 | Palestrant |
| 5,873,835 A | 2/1999 | Hastings |
| 5,902,248 A | 5/1999 | Millar et al. |
| 5,964,714 A | 10/1999 | Lafontaine |
| 6,033,366 A | 3/2000 | Brockway |
| 6,056,719 A | 5/2000 | Mickley |
| 6,089,103 A | 7/2000 | Smith |
| 6,106,476 A | 8/2000 | Corl et al. |
| 6,106,486 A | 8/2000 | Tenerz et al. |
| 6,112,598 A | 9/2000 | Tenerz et al. |
| 6,142,958 A | 11/2000 | Hammarstrom et al. |
| 6,167,763 B1 | 1/2001 | Tenerz et al. |
| 6,182,513 B1 | 2/2001 | Stemme et al. |
| 6,193,669 B1 | 2/2001 | Degany |
| 6,224,585 B1 | 5/2001 | Pfeiffer |
| 6,248,083 B1 | 6/2001 | Smith et al. |
| 6,296,615 B1 | 10/2001 | Brockway et al. |
| 6,312,380 B1 | 10/2001 | Brockway et al. |
| 6,336,906 B1 | 1/2002 | Hammarstrom et al. |
| 6,354,999 B1 | 3/2002 | Dgany |
| 6,379,308 B1 | 4/2002 | Brockway |
| 6,394,986 B1 | 5/2002 | Millar |
| 6,409,677 B1 | 6/2002 | Tulkki |
| 6,471,656 B1 | 10/2002 | Shalman et al. |
| 6,517,481 B2 | 2/2003 | Hoek et al. |
| 6,546,804 B2 | 4/2003 | Stemme et al. |
| 6,551,250 B2 | 4/2003 | Khalil |
| 6,565,514 B2 | 5/2003 | Svanerudh et al. |
| 6,585,660 B2 | 7/2003 | Dorando et al. |
| 6,615,067 B2 | 9/2003 | Hoek et al. |
| 6,615,667 B2 | 9/2003 | Smith |
| 6,659,957 B1 | 12/2003 | Verdi et al. |
| 6,659,959 B2 | 12/2003 | Brockway et al. |
| 6,663,570 B2 | 12/2003 | Mott et al. |
| 6,716,178 B1 | 4/2004 | Kilpatrick et al. |
| 6,733,459 B1 | 5/2004 | Atsumi |
| 6,754,608 B2 | 6/2004 | Svanrudh et al. |
| 6,767,327 B1 | 7/2004 | Corl et al. |
| 6,821,287 B1 | 11/2004 | Jang |
| 6,868,736 B2 | 3/2005 | Sawatari et al. |
| 6,926,674 B2 | 8/2005 | Tenerz et al. |
| 6,938,474 B2 | 9/2005 | Melvas |
| 6,966,890 B2 | 11/2005 | Coyle et al. |
| 6,974,422 B1 | 12/2005 | Millar |
| 6,976,965 B2 | 12/2005 | Corl et al. |
| 6,993,974 B2 | 2/2006 | Tenerz et al. |
| 6,994,695 B1 | 2/2006 | Millar |
| 7,017,416 B1 | 3/2006 | Liu et al. |
| 7,021,152 B2 | 4/2006 | Tenerz |
| 7,025,727 B2 | 4/2006 | Brockway |
| 7,060,038 B2 | 6/2006 | Letort et al. |
| 7,097,620 B2 | 8/2006 | Corl et al. |
| 7,112,170 B2 | 9/2006 | Schock et al. |
| 7,134,994 B2 | 11/2006 | Alpert et al. |
| 7,137,953 B2 | 11/2006 | Eigler et al. |
| 7,211,048 B1 | 5/2007 | Najafi |
| 7,222,539 B2 | 5/2007 | Tulkki |
| 7,229,403 B2 | 6/2007 | Schock |
| 7,245,789 B2 | 7/2007 | Bates et al. |
| 7,263,894 B2 | 9/2007 | Tenerz |
| 7,274,956 B2 | 9/2007 | Mott et al. |
| RE39,863 E | 10/2007 | Smith |
| 7,294,117 B2 | 11/2007 | Provost-tine et al. |
| 7,329,223 B1 | 2/2008 | Ainsworth et al. |
| 7,331,236 B2 | 2/2008 | Smith et al. |
| 7,343,811 B2 | 3/2008 | Tenerz et al. |
| 7,347,822 B2 | 3/2008 | Brockway |
| 7,447,388 B2 | 11/2008 | Bates et al. |
| 7,450,989 B2 | 11/2008 | Svanerudh |
| 7,454,244 B2 | 11/2008 | Kassab et al. |
| 7,458,938 B2 | 12/2008 | Patel et al. |
| 7,472,601 B1 | 1/2009 | Tenerz et al. |
| 7,481,774 B2 | 1/2009 | Brockway et al. |
| 7,527,594 B2 | 5/2009 | Vardi et al. |
| 7,532,920 B1 | 5/2009 | Ainsworth et al. |
| 7,599,588 B2 | 10/2009 | Eberle et al. |
| 7,645,233 B2 | 1/2010 | Tulkki et al. |
| 7,660,492 B2 | 2/2010 | Bates et al. |
| 7,724,148 B2 | 5/2010 | Samuelsson et al. |
| 7,731,664 B1 | 6/2010 | Millar |
| 7,775,988 B2 | 8/2010 | Pijls |
| 7,783,338 B2 | 8/2010 | Ainsworth et al. |
| 7,837,650 B1 | 11/2010 | Cox et al. |
| 7,881,573 B2 | 2/2011 | Eberle et al. |
| 7,931,603 B2 | 4/2011 | Von Malmborg et al. |
| 7,946,997 B2 | 5/2011 | Hubinette |
| 7,967,761 B2 | 6/2011 | Smith |
| 7,967,762 B2 | 6/2011 | Corl et al. |
| 7,998,089 B2 | 8/2011 | Smith |
| 8,025,623 B1 | 9/2011 | Millar |
| 8,029,447 B2 | 10/2011 | Kanz et al. |
| 8,059,923 B2 | 11/2011 | Bates et al. |
| 8,140,146 B2 | 3/2012 | Kim et al. |
| 8,157,742 B2 | 4/2012 | Taylor |
| 8,162,856 B2 | 4/2012 | Williams et al. |
| 8,174,395 B2 | 5/2012 | Samuelsson |
| 8,187,195 B2 | 5/2012 | Tulkki |
| 8,216,151 B2 | 7/2012 | Smith |
| 8,231,537 B2 | 7/2012 | Ahmed et al. |
| 8,249,815 B2 | 8/2012 | Taylor |
| 8,277,386 B2 | 10/2012 | Ahmed et al. |
| 8,282,565 B2 | 10/2012 | Mahapatra et al. |
| 8,298,156 B2 | 10/2012 | Manstrom et al. |
| 8,311,747 B2 | 11/2012 | Taylor |
| 8,311,748 B2 | 11/2012 | Taylor et al. |
| 8,311,750 B2 | 11/2012 | Taylor |
| 8,315,812 B2 | 11/2012 | Taylor |
| 8,315,813 B2 | 11/2012 | Taylor et al. |
| 8,315,814 B2 | 11/2012 | Taylor et al. |
| 8,317,715 B2 | 11/2012 | Belleville et al. |
| 8,320,723 B2 | 11/2012 | Eberle et al. |
| 8,321,150 B2 | 11/2012 | Taylor |
| 8,410,940 B2 | 4/2013 | Samuelsson |
| 8,419,647 B2 | 4/2013 | Corl et al. |
| 8,419,648 B2 | 4/2013 | Corl et al. |
| 8,461,997 B2 | 6/2013 | Samuelsson |
| 8,485,985 B2 | 7/2013 | Manstrom |
| 8,556,520 B2 | 10/2013 | Elenbaas et al. |
| 8,562,537 B2 | 10/2013 | Alpert et al. |
| 8,636,659 B2 | 1/2014 | Alpert et al. |

(56) References Cited

U.S. PATENT DOCUMENTS

| | | |
|---|---|---|
| 8,641,639 B2 | 2/2014 | Manstrom |
| 8,696,584 B2 | 4/2014 | Kassab |
| 8,698,638 B2 | 4/2014 | Samuelsson et al. |
| 8,714,021 B2 | 5/2014 | Gamage |
| 8,797,155 B2 | 8/2014 | Huennekens et al. |
| 8,857,264 B2 | 10/2014 | Gamage |
| 8,860,851 B2 | 10/2014 | Goma et al. |
| 8,958,863 B2 | 2/2015 | Huennekens et al. |
| 8,977,336 B2 | 3/2015 | Huennekens et al. |
| 8,998,823 B2 | 4/2015 | Manstrom et al. |
| 9,011,342 B2 | 4/2015 | Manstrom et al. |
| 9,113,843 B2 | 8/2015 | Manstrom et al. |
| 9,186,072 B2 | 11/2015 | Manstrom et al. |
| 9,220,461 B2 | 12/2015 | Samuelsson et al. |
| 9,259,161 B2 | 2/2016 | Suchecki et al. |
| 9,289,137 B2 | 3/2016 | Corl |
| 9,314,584 B1 | 4/2016 | Riley et al. |
| 9,332,916 B2 | 5/2016 | Kassab |
| 9,339,348 B2 | 5/2016 | Davies et al. |
| 2001/0051769 A1 | 12/2001 | Hoek et al. |
| 2002/0013527 A1 | 1/2002 | Hoek et al. |
| 2002/0035331 A1 | 3/2002 | Brockway et al. |
| 2002/0059827 A1 | 5/2002 | Smith |
| 2002/0065472 A1 | 5/2002 | Brockway et al. |
| 2002/0072880 A1 | 6/2002 | Svanerudh et al. |
| 2002/0157473 A1 | 10/2002 | Stemme et al. |
| 2002/0173724 A1 | 11/2002 | Dorando et al. |
| 2003/0018273 A1 | 1/2003 | Corl et al. |
| 2003/0032886 A1 | 2/2003 | Dgany et al. |
| 2003/0033095 A1 | 2/2003 | Svanerudh et al. |
| 2003/0040674 A1 | 2/2003 | Corl et al. |
| 2003/0159518 A1 | 8/2003 | Sawatari et al. |
| 2003/0163052 A1 | 8/2003 | Mott et al. |
| 2003/0176850 A1 | 9/2003 | Melvas |
| 2003/0195428 A1 | 10/2003 | Brockway et al. |
| 2003/0216621 A1 | 11/2003 | Alpert et al. |
| 2004/0067000 A1 | 4/2004 | Bates et al. |
| 2004/0082844 A1 | 4/2004 | Vardi et al. |
| 2004/0082866 A1 | 4/2004 | Mott et al. |
| 2004/0116816 A1 | 6/2004 | Tenerz et al. |
| 2004/0143240 A1 | 7/2004 | Armstrong et al. |
| 2004/0143261 A1 | 7/2004 | Hartley et al. |
| 2004/0157790 A1 | 8/2004 | Herweijer et al. |
| 2004/0162548 A1 | 8/2004 | Reiser |
| 2004/0167385 A1 | 8/2004 | Rioux et al. |
| 2004/0176790 A1 | 9/2004 | Coyle |
| 2004/0230131 A1 | 11/2004 | Kassab et al. |
| 2004/0254442 A1 | 12/2004 | Williams et al. |
| 2005/0000294 A1 | 1/2005 | Tenerz et al. |
| 2005/0011272 A1 | 1/2005 | Tenerz |
| 2005/0043670 A1 | 2/2005 | Rosenberg |
| 2005/0049451 A1 | 3/2005 | Schock et al. |
| 2005/0187487 A1 | 8/2005 | Azizkhan |
| 2005/0268724 A1 | 12/2005 | Tenerz |
| 2005/0268725 A1 | 12/2005 | Tulkki |
| 2006/0052700 A1 | 3/2006 | Svanerudh |
| 2006/0074318 A1 | 4/2006 | Ahmed et al. |
| 2006/0094966 A1 | 5/2006 | Brockway et al. |
| 2006/0094982 A1 | 5/2006 | Corl et al. |
| 2006/0207335 A1 | 9/2006 | Tenerz et al. |
| 2006/0241505 A1 | 10/2006 | Ahmed et al. |
| 2006/0287569 A1 | 12/2006 | Schock et al. |
| 2007/0060820 A1* | 3/2007 | Lofgren .............. A61B 5/0215 600/481 |
| 2007/0060822 A1 | 3/2007 | Alpert et al. |
| 2007/0078352 A1 | 4/2007 | Pijls |
| 2007/0106142 A1 | 5/2007 | Von Malmborg et al. |
| 2007/0106165 A1 | 5/2007 | Tulkki |
| 2007/0116408 A1 | 5/2007 | Eberle et al. |
| 2007/0133925 A1 | 6/2007 | Bates et al. |
| 2007/0135718 A1 | 6/2007 | Corl et al. |
| 2007/0191717 A1 | 8/2007 | Rosen et al. |
| 2007/0220986 A1 | 9/2007 | Smith et al. |
| 2007/0255144 A1 | 11/2007 | Tulkki et al. |
| 2007/0255145 A1 | 11/2007 | Smith |
| 2008/0119739 A1 | 5/2008 | Vardi et al. |
| 2008/0119758 A1 | 5/2008 | Samuelsson et al. |
| 2008/0132806 A1 | 6/2008 | Smith |
| 2008/0139897 A1 | 6/2008 | Ainsworth et al. |
| 2008/0146993 A1* | 6/2008 | Krishna .............. A61M 5/142 604/65 |
| 2008/0200770 A1 | 8/2008 | Hubinette |
| 2008/0255471 A1 | 10/2008 | Maghavi et al. |
| 2008/0269572 A1 | 10/2008 | Kanz et al. |
| 2009/0059727 A1 | 3/2009 | Bates et al. |
| 2009/0082678 A1 | 3/2009 | Smith |
| 2009/0088609 A1 | 4/2009 | Schmitz-Rode et al. |
| 2009/0088650 A1 | 4/2009 | Corl |
| 2009/0124880 A1 | 5/2009 | Smith |
| 2009/0125007 A1 | 5/2009 | Splinter |
| 2009/0248049 A1 | 10/2009 | Perkins |
| 2009/0281394 A1 | 11/2009 | Russell et al. |
| 2010/0014810 A1 | 1/2010 | Eberle et al. |
| 2010/0087732 A1 | 4/2010 | Eberle et al. |
| 2010/0109104 A1 | 5/2010 | Tiensuu et al. |
| 2010/0113942 A1 | 5/2010 | Eberle |
| 2010/0135111 A1 | 6/2010 | Bates et al. |
| 2010/0152607 A1 | 6/2010 | Kassab |
| 2010/0234698 A1 | 9/2010 | Manstrom et al. |
| 2010/0241008 A1 | 9/2010 | Belleville et al. |
| 2010/0280330 A1 | 11/2010 | Samuelsson et al. |
| 2010/0286536 A1 | 11/2010 | Samuelsson et al. |
| 2010/0286537 A1 | 11/2010 | Pijls |
| 2011/0004198 A1 | 1/2011 | Hoch |
| 2011/0060229 A1 | 3/2011 | Hulvershorn |
| 2011/0066047 A1 | 3/2011 | Belleville et al. |
| 2011/0071407 A1 | 3/2011 | Hubinette et al. |
| 2011/0083521 A1 | 4/2011 | Hollander et al. |
| 2011/0123154 A1 | 5/2011 | Eberle et al. |
| 2011/0137140 A1 | 6/2011 | Tearney et al. |
| 2011/0178383 A1 | 7/2011 | Kassab |
| 2011/0178417 A1 | 7/2011 | Kassab |
| 2011/0196255 A1 | 8/2011 | Kassab |
| 2011/0245693 A1 | 10/2011 | Hastings et al. |
| 2011/0251497 A1 | 10/2011 | Corl et al. |
| 2011/0306867 A1 | 12/2011 | Gopinathan et al. |
| 2011/0319773 A1 | 12/2011 | Kanz et al. |
| 2012/0053918 A1 | 3/2012 | Taylor |
| 2012/0071782 A1 | 3/2012 | Patil et al. |
| 2012/0072190 A1 | 3/2012 | Sharma et al. |
| 2012/0101355 A1 | 4/2012 | Gopinathan et al. |
| 2012/0101369 A1 | 4/2012 | Patil et al. |
| 2012/0108943 A1 | 5/2012 | Bates et al. |
| 2012/0136244 A1 | 5/2012 | Manstrom et al. |
| 2012/0172731 A1 | 7/2012 | Smith |
| 2012/0172732 A1 | 7/2012 | Meyer |
| 2012/0203118 A1 | 8/2012 | Samuelsson et al. |
| 2012/0220836 A1 | 8/2012 | Alpert et al. |
| 2012/0220837 A1 | 8/2012 | Alpert et al. |
| 2012/0220883 A1 | 8/2012 | Manstrom et al. |
| 2012/0227505 A1 | 9/2012 | Belleville et al. |
| 2012/0271178 A1 | 10/2012 | Smith |
| 2012/0278008 A1 | 11/2012 | Davies et al. |
| 2012/0316419 A1 | 12/2012 | Chevalier |
| 2013/0015975 A1 | 1/2013 | Huennekens et al. |
| 2013/0023762 A1 | 1/2013 | Huennekens et al. |
| 2013/0023763 A1 | 1/2013 | Huennekens et al. |
| 2013/0046190 A1 | 2/2013 | Davies |
| 2013/0060133 A1 | 3/2013 | Kassab et al. |
| 2013/0090555 A1 | 4/2013 | Kassab |
| 2013/0096409 A1 | 4/2013 | Hiltner et al. |
| 2013/0109980 A1 | 5/2013 | Teo |
| 2013/0116579 A1 | 5/2013 | Svanerudh |
| 2013/0131523 A1 | 5/2013 | Suchecki et al. |
| 2013/0190633 A1 | 7/2013 | Dorando et al. |
| 2013/0216481 A1* | 8/2013 | Rosenmeier ....... A61K 51/0476 424/9.1 |
| 2013/0303914 A1 | 11/2013 | Hiltner et al. |
| 2013/0324864 A1 | 12/2013 | Manstrom |
| 2014/0024235 A1 | 1/2014 | Russell |
| 2014/0024950 A1 | 1/2014 | Hiltner et al. |
| 2014/0086461 A1 | 3/2014 | Yao et al. |
| 2014/0180140 A1 | 6/2014 | Alpert |
| 2014/0180141 A1 | 6/2014 | Millett |

(56) References Cited

U.S. PATENT DOCUMENTS

| | | | |
|---|---|---|---|
| 2014/0187980 A1 | 7/2014 | Burkett |
| 2014/0187984 A1 | 7/2014 | Burkett |
| 2014/0276142 A1 | 9/2014 | Dorando |
| 2014/0379269 A1 | 12/2014 | Schmitt |
| 2015/0032011 A1 | 1/2015 | McGowan et al. |
| 2015/0074995 A1 | 3/2015 | Patil et al. |
| 2015/0105673 A1 | 4/2015 | Gregorich |
| 2015/0112191 A1 | 4/2015 | Gilboa et al. |
| 2015/0141853 A1 | 5/2015 | Miller et al. |
| 2015/0148693 A1 | 5/2015 | Burkett |
| 2015/0157216 A1 | 6/2015 | Stigall et al. |
| 2015/0173722 A1 | 6/2015 | Huennekens et al. |
| 2015/0265167 A1 | 9/2015 | McGowan et al. |
| 2015/0272449 A1 | 10/2015 | Meyer |
| 2015/0282765 A1 | 10/2015 | Goshen et al. |
| 2015/0313479 A1 | 11/2015 | Stigall et al. |
| 2015/0359438 A1 | 12/2015 | McCaffrey et al. |
| 2015/0359439 A1 | 12/2015 | Manstrom et al. |
| 2016/0022153 A1 | 1/2016 | Dorando |
| 2016/0066802 A1 | 3/2016 | Keller |
| 2016/0106321 A1 | 4/2016 | Sharma et al. |

FOREIGN PATENT DOCUMENTS

| | | | |
|---|---|---|---|
| EP | 1658808 | 8/1995 | |
| EP | 1260175 | 11/2002 | |
| EP | 1493381 | 1/2005 | |
| EP | 1165171 | 3/2005 | |
| EP | 1702641 | 9/2006 | |
| EP | 1498068 | 3/2007 | |
| EP | 01419796 B1 | 3/2008 | |
| JP | 10033488 | 2/1998 | |
| JP | 10137199 | 5/1998 | |
| JP | 2000-333913 | 12/2000 | |
| JP | 2004-194996 | 7/2004 | |
| JP | 2005-3638066 | 1/2005 | |
| JP | 2005-095603 | 4/2005 | |
| JP | 2005-3705458 | 8/2005 | |
| JP | 2006-204378 | 8/2006 | |
| NL | 2009285 | 8/2012 | |
| WO | WO1997/000641 | 1/1997 | |
| WO | WO1999/058059 | 11/1999 | |
| WO | WO2003/022122 | 3/2003 | |
| WO | WO2006/037082 | 4/2006 | |
| WO | WO2006/0117154 | 11/2006 | |
| WO | WO2011/0120565 | 10/2011 | |
| WO | WO 2011161212 A1 * | 12/2011 | ......... A61B 5/02007 |
| WO | WO2012093260 | 7/2012 | |
| WO | WO2012173697 | 12/2012 | |
| WO | WO2013061281 | 5/2013 | |
| WO | WO2014/025255 | 2/2014 | |
| WO | WO2014176448 | 10/2014 | |
| WO | WO2015/150128 | 10/2015 | |
| WO | WO2016/001017 | 1/2016 | |

OTHER PUBLICATIONS

PCT/US2014/064999, PCT International Search Report and The Written Opinion, dated Jan. 21, 2015.

* cited by examiner

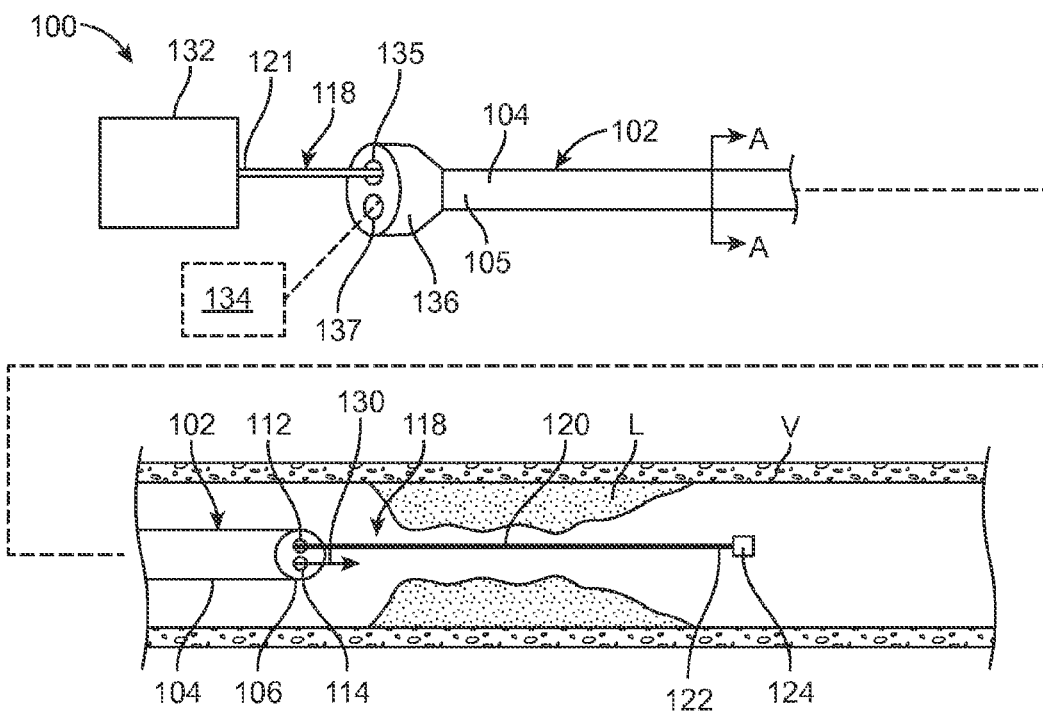
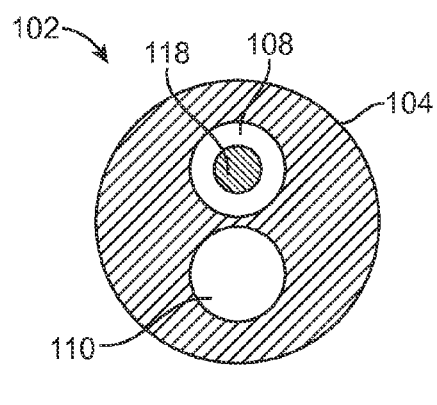 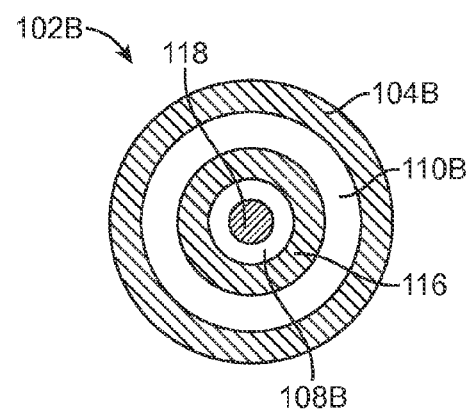
FIG. 1
FIG. 1A    FIG. 1B

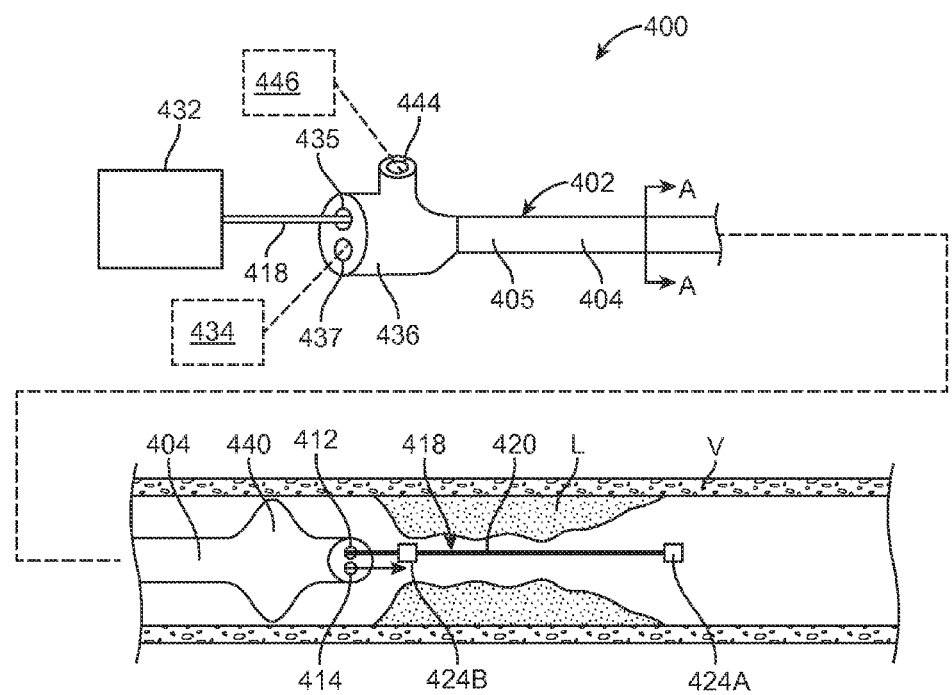
FIG. 4
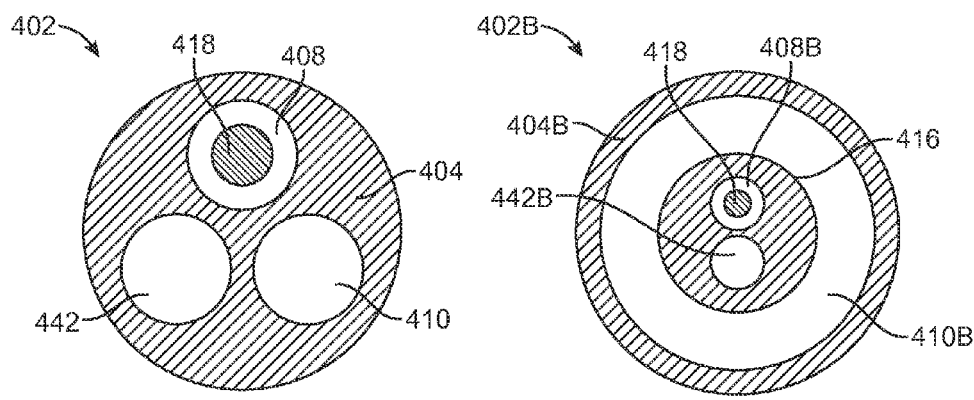
FIG. 4A
FIG. 4B

SYSTEMS AND METHODS FOR DETERMINING FRACTIONAL FLOW RESERVE WITHOUT ADENOSINE OR OTHER PHARMALOGICAL AGENT

FIELD OF THE INVENTION

The invention methods and systems for determining a pressure gradient across a lesion of a vessel.

BACKGROUND OF THE INVENTION

The severity of a stenosis or lesion in a blood vessel may be assessed by obtaining proximal and distal pressure measurements relative to the given stenosis and using those measurements for calculating a value of the Fractional Flow Reserve (FFR). FFR is defined as the ratio of a first pressure measurement (Pd) taken on the distal side of the stenosis and to a second pressure measurement taken on the proximal side of the lesion usually within the aorta (Pa). Conventionally, a sensor placed on the distal portion of a flexible interventional device, such as a guidewire, is utilized to obtain the first pressure measurement Pd, while an external pressure transducer is fluidly connected via tubing to a guide catheter for obtaining the second or aortic (AO) pressure measurement Pa. AO pressure is measured in various coronary catheterisation procedures and typically is measured via an external pressure transducer connected to the proximal end of a guide catheter. Once the guide catheter is positioned in situ, the lumen of the guide catheter fills with blood and the pressure of blood filling the lumen is equal to the pressure of the blood at the distal tip of the guide catheter. Tubing that fluidly connects the proximal end of the guide catheter to the external pressure transducer also fills with blood such that the external pressure transducer records or measures the pressure of the blood. Calculation of the FFR value provides a lesion specific index of the functional severity of the stenosis in order to determine whether the blockage limits blood flow within the vessel to an extent that treatment is needed. An optimal or normal value of FFR in a healthy vessel is 1.00, while values less than about 0.80 are generally deemed significant and in need of an interventional treatment. Common interventional treatment options include balloon angioplasty and/or stent implantation.

Blood flow through the coronary arteries is affected by fluctuations in the pressure arising proximally of the lesion, e.g., in the aorta, as well as fluctuations in pressure arising distally of the lesion, e.g., in the microcirculation. Accordingly, it is not possible to accurately assess the severity of a coronary lesion by simply measuring the pressure differential across the lesion because the pressure measurement taken on the distal side of the lesion is not purely a residual of the pressure transmitted from the aortic end of the vessel. As a result, for an effective calculation of FFR within the coronary arteries, it is necessary to reduce the vascular resistance within the vessel. Currently, pharmacological hyperemic agents, in particular Adenosine, are administered to reduce and stabilize the resistance within the coronary arteries. These potent vasodilator agents reduce the dramatic fluctuation in resistance to obtain a relatively stable and minimal resistance value.

However, the administration of pharmacological hyperemic agents is not always possible or advisable. In some countries, pharmacological hyperemic agents such as adenosine are expensive and time consuming to obtain when delivered intravenously (IV). In that regard, IV-delivered adenosine is generally mixed on a case-by-case basis in the hospital pharmacy. It can take a significant amount of time and effort to get the adenosine prepared and delivered to the operating area. These logistic hurdles can impact a physician's decision to use FFR. In addition, some patients cannot use hyperemic agents due to conditions such as asthma, severe COPD, hypotension, bradycardia, low cardiac ejection fraction, recent myocardial infarction, and/or other factors that prevent the administration of pharmacological hyperemic agents. Further, even if not prohibited, many patients find the administration of pharmacological hyperemic agents to be uncomfortable because vasodilation recreates the symptoms of angina, which is only compounded by the fact that the pharmacological hyperemic agent may need to be applied multiple times during the course of a procedure to obtain FFR measurements.

There is a need in the art for alternative devices and methods for obtaining FFR measurements without the need for a pharmacological hyperemic agent.

BRIEF SUMMARY OF THE INVENTION

Embodiments hereof relate to a method of determining a pressure gradient across a lesion of a vessel. A pressure-sensing instrument having at least a first pressure sensor at a distal portion thereof is percutaneously delivered through a vasculature until the first pressure sensor is positioned adjacent to and distal to the lesion. A catheter is distally advanced over the pressure-sensing instrument via a first lumen of the catheter until a distal end of the catheter is positioned adjacent to and proximal to the lesion. A non-pharmacologic fluid is injected through a second lumen of the catheter and across the lesion, wherein injection of the non-pharmacologic fluid increases a flow rate across a portion of the vessel including the lesion. A distal pressure measurement is measured at a location distal to the lesion with the first pressure sensor of the pressure-sensing instrument, wherein the step of obtaining the distal pressure measurement occurs while the flow rate across the lesion is increased. The distal pressure measurement and a proximal pressure representative of the pressure at a location proximal to the lesion are used to determine the pressure gradient across the lesion.

In another embodiment hereof, a pressure-sensing instrument having at least a first pressure sensor at a distal portion thereof is percutaneously delivered through a vasculature until the first pressure sensor is positioned adjacent to and distal to the lesion. A catheter is distally advanced over the pressure-sensing instrument via a first lumen of the catheter until a distal end of the catheter is positioned adjacent to and proximal to the lesion. A balloon is inflated at a distal portion of the catheter to block blood flow across the lesion. A non-pharmacologic fluid is injected through a second lumen of the catheter and across the lesion, wherein injection of the non-pharmacologic fluid increases a flow rate across a portion of the vessel including the lesion. A distal pressure measurement is measured at a location distal to the lesion with the first pressure sensor of the pressure-sensing instrument. A proximal pressure measurement is measured at a location proximal to the lesion, wherein the steps of obtaining distal and proximal pressure measurements are performed while the portion of the vessel including the lesion has an increased flow rate there-through due to injection of the non-pharmacologic fluid. The distal pressure measurement and the proximal pressure measurement are used to determine the pressure gradient across the lesion.

Embodiments hereof also relate to a system for determining a pressure gradient across a lesion of a vessel. The system includes a catheter and a pressure-sensing instrument. The catheter has at least a first lumen configured to slidingly receive a pressure-sensing instrument and a second lumen configured to deliver an injectable fluid out of a distal end of the catheter from a proximal end of the catheter. The pressure-sensing instrument is slidingly disposed through the first lumen of the catheter. The pressure-sensing instrument has at least a first pressure sensor at a distal portion thereof, wherein the first pressure sensor is configured to obtain a pressure measurement for use in determining the pressure gradient across the lesion.

BRIEF DESCRIPTION OF DRAWINGS

The foregoing and other features and advantages of the invention will be apparent from the following description of embodiments hereof as illustrated in the accompanying drawings. The accompanying drawings, which are incorporated herein and form a part of the specification, further serve to explain the principles of the invention and to enable a person skilled in the pertinent art to make and use the invention. The drawings are not to scale.

FIG. 1 is an illustration of a system for measuring FFR with a distal portion thereof shown within a vessel including a lesion, the system including an injection catheter and a pressure-sensing guidewire having a sensor mounted thereon according to an embodiment hereof, wherein the system injects a non-pharmacologic fluid across the lesion to increase a flow rate there-through.

FIG. 1A is a cross-sectional view of the system taken along line A-A of FIG. 1.

FIG. 1B is a cross-sectional view of the system taken along line A-A of FIG. 1 according to another embodiment hereof.

FIG. 3 is an illustration of a distal portion of a system for measuring FFR within a vessel including a lesion, the system including an injection catheter and a pressure-sensing guidewire having two sensors mounted thereon according to another embodiment hereof, wherein the system injects a non-pharmacologic fluid across the lesion to increase a flow rate there-through.

FIG. 4 is an illustration of a system for measuring FFR with a distal portion thereof shown within a vessel including a lesion, the system including an injection balloon catheter and a pressure-sensing guidewire having two sensors mounted thereon according to another embodiment hereof, wherein the system injects a non-pharmacologic fluid across the lesion to increase a flow rate there-through.

FIG. 4A is a cross-sectional view taken along line A-A of FIG. 4.

FIG. 4B is a cross-sectional view taken along line A-A of FIG. 4 according to another embodiment hereof.

DETAILED DESCRIPTION OF THE INVENTION

Figure 2:
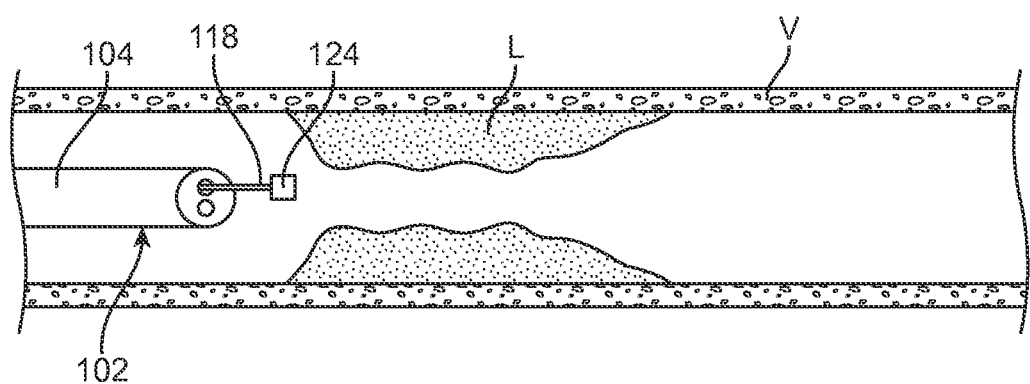
FIG. 2 is an illustration of the distal portion of the system of FIG. 1, wherein the system has been proximally retracted for obtaining a proximal pressure measurement.

Specific embodiments of the present invention are now described with reference to the figures, wherein like reference numbers indicate identical or functionally similar elements. The terms "distal" and "proximal" are used in the hollowing description with respect to a position or direction relative to the treating clinician. "Distal" or "distally" are a position distant from or in a direction away from the clinician, "Proximal" and "proximally" are a position near or in a direction toward the clinician.

The following detailed description is merely exemplary in nature and is not intended to limit the invention or the application and uses of the invention. Although the description of the invention is in the context of treatment of blood vessels such as the coronary arteries, the invention may also be used in any other body passageways where it is deemed useful such as but not limited to peripheral arteries, carotid arteries, renal arteries, and/or venous applications. Furthermore, there is no intention to be bound by any expressed or implied theory presented in the preceding technical field, background, brief summary or the following detailed description.

Embodiments hereof relate to a measurement system or assembly for determining a pressure gradient across a lesion of a vessel without requiring the use of a pharmacological hyperemic agent such as Adenosine or other vasodilator drugs. The measurement system includes at least an injection catheter and a pressure-sensing instrument or guidewire slidingly disposed through the catheter, the pressure-sensing guidewire including at least one pressure sensor configured to obtain a pressure measurement for use in determining the pressure gradient across the lesion. The catheter is configured to deliver or inject a non-pharmacological fluid, such as saline, across the lesion in order to increase a flow rate there-through, thereby simulating hyperemia without the use of a pharmacological hyperemic agent. Once an increased flow rate is achieved, the pressure sensor of the pressure-sensing guidewire may be utilized to measure the pressure gradient across the lesion in order to assess the severity of the lesion.

More particularly, with reference to FIGS. 1 and 1A, a measurement system 100 is shown with a proximal portion thereof extending outside of a patient and a distal portion thereof positioned in situ within a vessel V having a stenosis or lesion L. In an embodiment hereof, the vessel V is a blood vessel such as but not limited to a coronary artery. Lesion L is generally representative of any blockage or other structural arrangement that results in a restriction to the flow of fluid through the lumen of vessel V. Lesion L may be a result of plaque buildup, including without limitation plaque components such as fibrous, fibro-lipidic (fibro fatty), necrotic core, calcified (dense calcium), blood, fresh thrombus, and mature thrombus. Generally, the composition of lesion will depend on the type of vessel being evaluated. In that regard, it is understood that embodiments hereof are applicable to various types of blockage or other narrowing of a vessel that results in decreased fluid flow.

Measurement system 100 includes an injection catheter 102 and a pressure-sensing instrument or guidewire 118 slidingly disposed through the catheter. Distal portions of catheter 102 and pressure-sensing guidewire 118 are shown positioned in situ within a portion of vessel V in FIG. 1. Injection catheter 102 includes an elongated shaft 104 with a proximal end 105 and a distal end 106. With additional reference to the cross-sectional view of FIG. 1A, elongated shaft 104 defines two separate lumens, a first or guidewire lumen 108 and a second or fluid delivery lumen 110, extending parallel or side-by-side to each other for the entire length of elongated shaft 104. Although depicted as circular in cross-section, one or more lumen(s) of elongated shaft 104 may have any suitable cross-section including for example circular, elliptical, or crescent-shaped. The distal ends of first and second lumens 108, 110 are open and define distal ports 112, 114, respectively. First lumen 108 accommodates pressure-sensing guidewire 118 received through a first proximal port 135 of a hub 136 disposed at the proximal end 105 of elongated shaft 104, while second lumen 110 serves as a passageway to deliver a non-pharmacological fluid to lesion L from a second proximal port 137 of hub 136, through elongated shaft 104, and out of distal port 114. A pump or source 134 of the non-pharmacological fluid is shown extending from second proximal port 137. In the embodiment of FIG. 1A, elongated shaft 104 is formed by multi-lumen profile extrusion. However, other types of catheter construction are also amendable to the invention, such as, without limitation thereto, a dual lumen catheter formed by two coaxial shafts. For example, an alternate catheter construction is illustrated in FIG. 1B. Rather than including a single catheter shaft formed by multi-lumen extrusion, catheter 102B includes an outer shaft 104B and an inner shaft 116. A first or guidewire lumen 108B is defined by inner shaft 116, while a second or fluid delivery lumen 110B is defined by the annular space between outer shaft 104B and inner shaft 116.

Elongated shaft 104 may be formed of a polymeric material, non-exhaustive examples of which include polyethylene, PEBA, polyimide and/or combinations thereof, either blended or co-extruded. Optionally, the catheter shaft or some portion thereof may be firmed as a composite having a reinforcement material incorporated within a polymeric body in order to enhance strength and/or flexibility. Suitable reinforcement layers include braiding, wire mesh layers, embedded axial wires, embedded helical or circumferential wires, and the like. In one embodiment, for example, at least a proximal portion of elongated shaft 104 may be formed from a reinforced polymeric tube.

Pressure-sensing guidewire 118 has an elongated body 120 with a proximal end 121 and a distal end 122. At least one pressure sensor 124 is mounted adjacent to distal end 122 of the elongated body, and a computing device 132 is coupled to proximal end 121 of pressure-sensing guidewire 118. Proximal end 121 of pressure-sensing guidewire 118 may be coupled to computing device 132 via various communication pathways, including but not limited to one or more physical connections including electrical, optical, and/or fluid connections, a wireless connection, and/or combinations thereof. Accordingly, it is understood that additional components (e.g., cables, connectors, antennas, routers, switches, etc.) not illustrated in FIG. 1 may be included to facilitate communication between the proximal end of pressure-sensing guidewire 118 and computing device 132. In an embodiment hereof, pressure sensor 124 is mounted proximally from distal end 122 of the elongated body. Pressure sensor 124 is configured to obtain a pressure measurement for use in determining a pressure gradient across the lesion L. The pressure sensor 124 may be a piezo-resistive pressure sensor, a piezo-electric pressure sensor, a capacitive pressure sensor, an electromagnetic pressure sensor, a fluid column, an optical pressure sensor, and/or combinations thereof. Generally, guidewire 118 is sized such that it can be positioned through lesion L without significantly impacting fluid flow across the lesion, which would impact the distal pressure measurement or reading. Accordingly, in one embodiment, pressure-sensing guidewire 118 has an outer diameter of 0.014" or less. However, the measurement system 100 may utilize any type of elongated pressure-sensing instrument having a pressure sensor mounted at a distal portion thereof, such as but not limited to a microcatheter or catheter, and thereby have a larger outer diameter than that described with respect to pressure-sensing guidewire 118.

Figure 3:
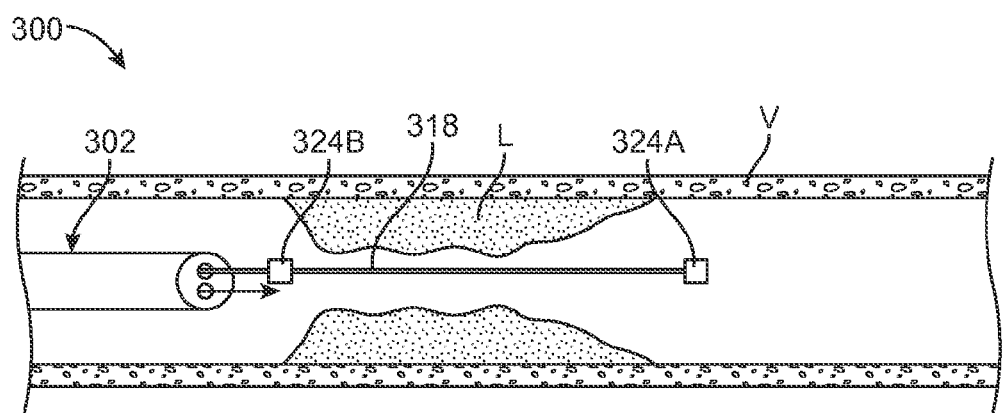

As will be explained in more detail herein, measurement system 100 is utilized for determining a pressure gradient across a lesion of a vessel from a distal pressure measurement and the proximal pressure measurement. In the embodiment of FIGS. 1-2, pressure sensor 124 is utilized for obtaining both the distal pressure measurement and the proximal pressure measurement in a non-simultaneous, sequential manner. However, as will be apparent from the additional embodiments described herein, there are various possible ways for obtaining the proximal pressure measurement. In one embodiment hereof, as shown in FIG. 3 described in more detail below, the pressure-sensing guidewire may include two pressure sensors for obtaining the proximal pressure measurement in a simultaneous manner. In another embodiment hereof, described in more detail below, the proximal pressure measurement may be obtained via an external pressure transducer that is fluidly connected via tubing to a guide catheter. In another embodiment hereof, described in more detail below, known or input parameters such as inlet flow rate and/or inlet pressure may be utilized as the proximal pressure.

A method of using measuring system 100 to determine a pressure gradient across a lesion of a vessel will now be described with reference to FIGS. 1-2. A distal portion of measurement system 100 is first positioned within vessel V as shown in FIG. 1. More particularly, a guiding catheter (not shown in FIG. 1) is first inserted through an incision (not shown) and into a femoral artery of a patient. Pressure-sensing guidewire 118 may be normalized or zeroed to atmospheric pressure and then is introduced into the guide catheter. Pressure-sensing guidewire 118 is then advanced out of the end of the guide catheter and maneuvered through the vasculature into a specific or target vessel V until pressure sensor 124 is positioned adjacent to and distal to (or downstream of) the lesion L. Injection catheter 102 is delivered by a clinician by threading or distally advancing catheter 102 over pressure-sensing guidewire 118 via first lumen 108 until distal end 106 of the catheter is outside of the guide catheter and is positioned adjacent to and proximal to (or upstream of) the lesion L. Although described as tracking injection catheter 102 over previously positioned pressure-sensing guidewire 118, it should be understood that injection catheter 102 and pressure-sensing guidewire 118 may be simultaneously advanced to the target lesion. As another alternative, a conventional guidewire (not shown) may be used to locate lesion L and infusion catheter 102 may thereafter be threaded over this conventional guidewire, which subsequently is replaced by pressure-sensing guidewire 118.

As shown in FIG. 1, once the components of measurement system 100 are positioned as desired, a non-pharmacologic fluid which is represented by directional arrow 130 is injected through second lumen 110 of injection catheter 102 and across lesion L. "Non-pharmacologic fluid" as used herein includes a biocompatible fluid or liquid that does not include a vasodilation drug or vasodilator, or otherwise stated a biocompatible fluid or liquid that does not include a chemical substance or agent which is medically effective to vasodilate a body lumen or vessel. In an embodiment hereof, the non-pharmacologic fluid is saline or blood. Saline as used herein refers to a 0.9% strength of sodium chloride (salt) solution in water, which has an osmolarity nearly the same as that of blood. Controlled injection of the non-pharmacologic fluid gradually increases flow rate across a portion of vessel V including lesion L, thereby simulating hyperemia which is required for subsequent calculations of the pressure gradient and/or FFR. More particularly, hyperemia is defined as the presence of an increased amount of blood in a part or organ. The pressure gradient and/or FFR calculations are a measure of the severity of a lesion and require distal and proximal pressure measurements during maximum hyperemia. While the composition of a pharmacological agent causes vasodilation or widening of a vessel in order to achieve hyperemia, injection of a non-pharmacologic fluid is mechanically increasing flow rate of fluid within the vessel in order to simulate hyperemia. The increased flow of non-pharmacologic fluid may result in dilation or widening of the vessel as a by-product thereof but the dilation is not a result of the composition or chemical agent of the injected fluid. Conversely, administration of a pharmacological fluid such as adenosine causes vasodilation of a vessel due to the composition or chemical agent(s) of the pharmacological fluid in order to cause hyperemia. The vasodilation or widening may result in increased blood flow rate as a by-product thereof. Thus, injection of the non-pharmacologic fluid and injection of a pharmacological fluid may result in similar increased flow rates, but advantageously use of the non-pharmacologic fluid eliminates and/or reduces side effects associated with the use of pharmacological agents.

Injection of the non-pharmacologic fluid occurs at an injection pressure sufficient to increase the flow rate across the portion of the vessel and thereby simulate hyperemia. In an embodiment hereof, the injection pressure of the non-pharmacologic fluid is relatively higher or faster than that of coronary flow. Notably, the injection of flow is controlled by the user because patients will differ as to when they will exhibit a hyperemic response. Although the particular injection pressure will vary according to an individual patient's needs, such injection pressures for the non-pharmacologic fluid are relatively higher than those utilized in the administration of pharmacologic fluids such as adenosine because the higher injection pressure causes or at least contributes to the increase in the flow rate. Conversely, injection pressures utilized in the administration of pharmacologic fluids such as adenosine are usually relatively lower or slower than that of coronary flow, and thus administration of pharmacologic fluids such as adenosine does not cause an increase in flow rate.

In addition, in order to sufficiently increase the flow rate across lesion L and thereby simulate hyperemia, distal end 106 of catheter 102 is advantageously positioned adjacent to and proximal to lesion L. Pharmacologic fluids such as adenosine are typically administered intravenously (IV), and thus disperse throughout the whole vascular system or at least a large portion of the vascular system beyond vessel V. In some cases, pharmacological fluids such as adenosine may be administered via an intracoronary approach in which it is delivered through a guide catheter having a distal end positioned at a spaced apart location from lesion L such as at an ostium or aortic location. When delivered via intracoronary approach, vasodilation from pharmacological fluids typically does not last very long and thus it often requires multiple administrations thereof in order to achieve the required vasodilation. Thus, due to both the spaced apart administration site and the multiple administrations thereof, pharmacological fluids often disperse throughout the whole vascular system or at least a large portion of the vascular system beyond vessel V even when delivered via intracoronary approach. Conversely, in embodiments hereof, administration of the non-pharmacologic fluid occurs directly adjacent to the proximal end of the lesion. With such direct or localized administration, the flow rate across the lesion is sufficiently increased relatively quickly, without widespread effects. Stated another way, such targeted administration minimizes the treatment area or zone and only increases the flow rate across a relatively short portion of vessel V, which includes lesion L. The flow or administration of the non-pharmacologic fluid may be either steady flow or pulsative flow.

After administration of the non-pharmacologic fluid causes the increased flow rate that simulates hyperemia, the distal pressure measurement is obtained via pressure sensor 124 of pressure-sensing guidewire 118, which is located at a location distal to lesion L as shown in FIG. 1. In order to obtain a pressure measurement from the pressure sensor, proximal end 121 of pressure-sensing guidewire 118 is coupled to computing device or interface 132, which is a device that transforms output signals from pressure sensor 124 into the distal pressure measurement of the medium surrounding the sensor. The distal pressure measurement is stored on or by computing device 132.

In an embodiment hereof, in order to ensure that administration of the non-pharmacologic fluid causes the increased flow rate that simulates hyperemia, distal pressure measurements may be continuously sensed and displayed via computing device 132 such that a physician or operator can monitor when such measurements equalize. More particularly, in one embodiment, it may be desirable to continuously inject the non-pharmacological fluid at a gradually increasing injection pressure until the distal pressure measurement levels out, thereby reflecting that a maximum increased flow rate has been achieved, or otherwise stated, that hyperemia has been simulated. Gradually or incrementally increasing the injection pressure accommodates the fact that the particular injection pressure required to simulate hyperemia will vary according to an individual patient's needs, and further ensures that the required increased flow rate is present for any final or determinative pressure measurements or calculations. Once the distal pressure measurement is constant or steady, thereby signaling hyperemia has been achieved under a certain injection pressure, the injection pressure of the non-pharmacologic fluid remains constant from this point of the procedure and the distal pressure measurement is stored on or by computing device 132.

Once the distal pressure measurement is obtained via pressure sensor 124, pressure-sensing guidewire 118 is proximally retracted or pulled back until pressure sensor 124 is positioned adjacent to and proximal to a proximal end of lesion L as shown in FIG. 2. During retraction of pressure-sensing guidewire 118, non-pharmacologic fluid is continuously injected in order to keep the flow rate across lesion L at a maximum rate that simulates hyperemia. Thus, the injection pressure of the non-pharmacologic fluid may remain constant, or may be varied if necessary, during movement of the guidewire in order to keep the increased flow rate across the lesion L constant or continuous. In an embodiment hereof, continuous sensing of pressure measurements may occur during pull-back or proximal retraction of pressure-sensing guidewire 118 in order to view inter-lesion pressure drop along the length of the lesion. More particularly, pressure gradient or pressure drop calculations may be continuously displayed while pressure sensor 124 of pressure-sensing guidewire 118 is repositioned from a position distal to lesion L to a position proximal to lesion L. Such continuous pressure calculations may provide additional information related to lesion morphology and significance of the stenosis to the operator.

After pressure-sensing guidewire 118 is positioned as desired, proximal to lesion L and distal to distal port 114 of injection catheter 102, pressure sensor 124 of pressure-sensing guidewire 118 is utilized to obtain the proximal pressure measurement. When obtaining the proximal pressure measurement, the injection pressure of the non-pharmacologic fluid remains constant such that the increased flow rate across lesion L is constant or continuous. Thus, the steps of obtaining both the distal and proximal pressure measurements, as well as any steps performed there-between such as pullback or retraction of pressure sensor 124, are performed during continued flow or administration of the non-pharmacologic fluid at an injection pressure sufficient to simulate hyperemia. As described with respect to the distal pressure measurement, computing device 132 transforms the output signals from pressure sensor 124 into the proximal pressure measurement of the medium surrounding the sensor. Thus, in this embodiment, pressure sensor 124 is utilized to collect or obtain distal and proximal pressure measurements via pull-back of pressure-sensing guidewire 118 in a non-simultaneous, sequential manner, without the need for a second pressure sensor. In an embodiment hereof, a calibration step in which pressure sensor 124 is normalized or zeroed to atmospheric pressure may occur after obtaining the distal pressure measurement but prior to obtaining the proximal pressure measurement.

The distal pressure measurement, which was previously stored by computing device 132, and the proximal pressure measurement are then used to determine the pressure gradient across the lesion. In an embodiment hereof, computing device 132 includes a processor and random access memory and is programmed to execute steps associated with the data acquisition and analysis. More particularly, computing device 132 is configured to calculate FFR and/or other pressure differential computations based on the pressure measurements or output signals obtained from pressure sensor 124. Accordingly, it is understood that steps related to data acquisition, data processing, instrument control, and/or other processing or control aspects may be implemented by computing device 132 using corresponding instructions stored on or in a non-transitory computer readable medium accessible by the computing device. For example, in another embodiment hereof, one or more of the data acquisition, data processing, instrument control, and/or other processing or control aspects may be performed on an executable program embedded into existing catheter lab infrastructure rather than a stand-alone computing device such as computing device 132. Computing device 132 may also include a display (not shown) which is configured to display various diagnostic information such as the distal pressure measurement, the proximal pressure measurement, FFR, other pressure differential computations, and/or additional diagnostic parameters.

In an embodiment hereof, the FFR parameter calculated herein with the use of a non-pharmacologic fluid may vary slightly from a FFR parameter calculated with the use of a pharmacologic fluid such as adenosine since the two FFR parameters are obtained via different methods. However, both FFR parameters accurately represent the pressure gradient across the lesion and have similar correlations and/or trends. In one embodiment hereof, computing device 132 may be configured to correlate or normalize the non-pharmacologic FFR parameter to a pharmacologic FFR parameter.

After calculation of FFR and/or other pressure differential computations, it may be desirable to temporarily stop flow or administration of the non-pharmacologic fluid. For example, it may be desirable to turn off flow or administration of the non-pharmacologic fluid for a pre-described time period, and then turn flow back on in order to perform or re-do the measurement steps again and thereby verify accuracy of the pressure differential computations at the same lesion L. In another embodiment, it may be desirable to turn off flow or administration of the non-pharmacologic fluid in order to relocate measurement system 100 to another lesion for evaluation thereof with the above-described measurement steps. In yet another embodiment, it may be desirable to turn off flow or administration of the non-pharmacologic fluid in order to implant a stent (during which there is no administration of the non-pharmacologic fluid) and then turn the flow back on to perform a post-stent FFR and/or other pressure differential computations.

As previously mentioned, there are various possible ways for obtaining the proximal pressure measurement. FIG. 3 illustrates another embodiment hereof in which the pressure-sensing guidewire may include two spaced-apart pressure sensors for obtaining the proximal and distal pressure measurements. More particularly, measurement system 300 includes an injection catheter 302 and a pressure-sensing guidewire 318, the distal portions thereof being positioned within a vessel V having a lesion L. Injection catheter 302 is similar to injection catheter 102. Pressure-sensing guidewire 318 is similar to pressure-sensing guidewire 118 except that pressure-sensing guidewire 318 includes a first pressure sensor 324A mounted at or adjacent to a distal end thereof for obtaining a distal pressure measurement as well as a second pressure sensor 324B for obtaining a proximal pressure measurement. Second pressure sensor 324B may be the same type of pressure sensor as first pressure sensor 324A, or may be a different type of pressure sensor. Each pressure sensor may be a piezo-resistive pressure sensor, a piezo-electric pressure sensor, a capacitive pressure sensor, an electromagnetic pressure sensor, a fluid column, an optical pressure sensor, and/or combinations thereof. The distal and proximal pressure measurements may be obtained via pressure sensors 324A, 324B, respectively, in a simultaneous manner after injection of the non-pharmacologic fluid through measurement catheter 302 and across lesion L. Since distal and proximal pressure measurements are obtained simultaneously in this embodiment, the FFR calculation is considered real-time FFR.

In another embodiment hereof, rather than measuring the proximal pressure with a pressure sensor, guidewire 118 is utilized to obtain the distal pressure measurement as described above with respect to FIG. 1 while known or input parameters such as inlet flow rate and/or inlet pressure may be utilized as the proximal pressure. In one example, the injection pressure or flow rate of the non-pharmacologic fluid is a known or input parameter and is sufficient to increase the flow rate across the portion of the vessel including the lesion. This injection pressure or flow rate may act as a surrogate for the proximal pressure measurement, that is the pressure proximal to lesion L and distal to distal port 114 of catheter 102, and may be utilized as a reference or standard pressure against the distal pressure measurement for purposes of calculating FFR and/or other pressure gradient calculations. Further, in another embodiment hereof, an aortic (AO) pressure measurement that may be obtained via an external pressure transducer fluidly connected via tubing to a guide catheter may be recorded and the additional pressure due to administration of the non-pharmacologic fluid may be interpolated or incorporated via computing device 132 to calculate a surrogate for the proximal pressure measurement.

In order to prevent backflow and ensure that all injected fluid is pumped through the lesion to increase flow rate, embodiments described herein may include an inflatable balloon to occlude blood flow proximal to the distal end of the injection catheter. More particularly, with reference to FIG. 4-4A, a measurement system 400 includes an injection catheter 402 and a pressure-sensing guidewire 418 slidingly disposed through the catheter. Distal portions of catheter 402 and pressure-sensing guidewire 418 are shown positioned within a vessel V having a lesion L in FIG. 4. Pressure-sensing guidewire 418 is similar to pressure-sensing guidewire 318 described above and includes an elongated body 420 with first and second pressure sensors 424A, 424B for obtaining distal and proximal pressure measurements.

Injection catheter 402 is similar to injection catheter 102 except that injection catheter 402 includes an inflatable compliant or semi-compliant balloon 440 at a distal portion of an elongated shaft 404. Balloon 440 is shown in its inflated or expanded configuration in FIG. 4. With reference to the cross-sectional view of FIG. 4A, elongated shaft 404 defines three separate lumens, a first or pressure-sensing guidewire lumen 408, a second or fluid delivery lumen 410, and an inflation lumen 442, extending parallel or side-by-side to each other. Although depicted as circular in cross-section, one or more lumen(s) of elongated shaft 404 may have any suitable cross-section including for example circular, elliptical, or crescent-shaped. Elongated shaft 404 includes one or more ports or passageways (not shown) formed therein such that inflation lumen 442 is in fluid communication with the interior volume of balloon 440. A hub 436 is disposed at a proximal end 405 of elongated shaft 404 includes an inflation port 444 which may be connected to a source 446 of inflation via a luer hub or other type of fitting (not shown) to allow inflation fluid received through inflation port 444 of hub 436 to be delivered to balloon 440. Similar to lumens 108, 110 of catheter 102 described above, the distal ends of first and second lumens 408, 410 are open and define distal ports 412, 414, respectively. First lumen 408 accommodates pressure-sensing guidewire 418 received through a first proximal port 435 of hub 436, while second lumen 410 serves as a passageway to deliver a non-pharmacological fluid to lesion L received through a second proximal port 437 of hub 436. In FIG. 4, a computing device 432 is coupled to a proximal end of pressure-sensing guidewire 418 and a pump or source 434 of the non-pharmacological fluid is shown extending from second proximal port 437. In addition to being utilized to prevent backflow during injection of the non-pharmacologic fluid, balloon 440 may also be re-inflated and utilized in an angioplasty treatment procedure if lesion L is deemed to require treatment.

In the embodiment of FIG. 4A, elongated shaft 404 is formed by multi-lumen profile extrusion. However, other types of catheter construction are also amendable to the invention, such as, without limitation thereto, a tri lumen catheter formed by two coaxial shafts. For example, an alternate catheter construction is illustrated in FIG. 4B. Rather than including a single catheter shaft formed by multi-lumen extrusion, catheter 402B has an over-the-wire (OTW) coaxial catheter configuration with an outer tubular component or shaft 404B and a dual lumen inner shaft 416. In the embodiment of FIG. 4B, inner shaft 416 is a dual lumen catheter shaft formed by multi-lumen extrusion and defines a first or guidewire lumen 408B and a second or fluid delivery lumen 410B. Inner shaft 416 extends coaxially within outer shaft 404B such that an annular inflation lumen 442B is defined between an inner surface of outer shaft 404B and an outer surface of inner shaft 416. Proximal ends of both outer shaft 404B and inner shaft 416 are coupled to hub 436, while a proximal end of balloon 440 is coupled to a distal end of outer shaft 404B and a distal end of balloon 440 is coupled to inner shaft 416. Additional types of catheter construction are also amendable to the invention, including a catheter having three coaxial shafts with an annular inflation lumen and an annular injection lumen.

While various embodiments according to the present invention have been described above, it should be understood that they have been presented by way of illustration and example only, and not limitation. It will be apparent to persons skilled in the relevant art that various changes in form and detail can be made therein without departing from the spirit and scope of the invention. For example, any embodiment herein may be modified to utilize a patient's own blood as the non-pharmacological fluid that increases flow rate across a lesion. Thus, the breadth and scope of the present invention should not be limited by any of the above-described exemplary embodiments, but should be defined only in accordance with the appended claims and their equivalents. It will also be understood that each feature of each embodiment discussed herein, and of each reference cited herein, can be used in combination with the features of any other embodiment. All patents and publications discussed herein are incorporated by reference herein in their entirety.

What is claimed is:

1. A method of determining a pressure gradient across a lesion of a vessel, the method comprising the steps of:
   percutaneously delivering a pressure-sensing instrument having at least a first pressure sensor at a distal portion thereof through a vasculature until the first pressure sensor is positioned adjacent to and distal to the lesion;
   distally advancing a catheter over the pressure-sensing instrument via a first lumen of the catheter until a distal end of the catheter is positioned adjacent to and proximal to the lesion;
   injecting a non-pharmacologic fluid at an injection pressure through a second lumen of the catheter and across the lesion;
   controlling the injection pressure to increase a flow rate across a portion of the vessel including the lesion;
   measuring a distal pressure at a location distal to the lesion with the first pressure sensor of the pressure-sensing instrument, wherein the step of measuring a distal pressure occurs while the flow rate across the lesion is increased and until the measured distal pressure becomes constant thereby simulating hyperemia across the lesion; and
   using the measured distal pressure and a proximal pressure representative of the pressure at a location proximal to the lesion to determine the pressure gradient across the lesion.

2. The method of claim 1, further comprising the step of:
   inflating a balloon at a distal portion of the catheter to block blood flow across the lesion, wherein the step of inflating the balloon occurs prior to the step of injecting non-pharmacologic fluid through the catheter and across the lesion.

3. The method of claim 1, wherein the non-pharmacologic fluid is blood or saline.

4. The method of claim 1, wherein the step of injecting a non-pharmacologic fluid includes gradually increasing the injection pressure of the non-pharmacologic fluid until injection of the non-pharmacologic fluid simulates hyperemia across the lesion and wherein the step of measuring a distal pressure is continuously performed during continued administration of the non-pharmacologic fluid at the injection pressure sufficient to simulate hyperemia across the lesion.

5. The method of claim 1, further comprising the step of:
   using the pressure gradient to determine a fractional flow reserve (FFR) calculation.

6. The method of claim 5, wherein the measured distal pressure and the proximal pressure are obtained simultaneously and the FFR calculation is a real-time calculation.

7. The method of claim 6, wherein the pressure-sensing instrument includes a second pressure sensor proximal to the first pressure sensor and the proximal pressure is obtained with the second pressure sensor.

8. The method of claim 5, wherein the measured distal pressure and the proximal pressure are obtained non-simultaneously.

9. The method of claim 8, further comprising the steps of:
proximally retracting the pressure-sensing instrument until the first pressure sensor is positioned adjacent to and proximal to the lesion, the step of proximally retracting the pressure-sensing instrument occurs after the step of measuring a distal pressure; and
measuring the proximal pressure with the first pressure sensor of the pressure-sensing instrument.

10. The method of claim 9, wherein during the step of proximally retracting the pressure-sensing instrument, the non-pharmacologic fluid is continuously injected in order to keep the flow rate across the lesion at a maximum rate that simulates hyperemia.

11. The method of claim 1, wherein the step of injecting a non-pharmacologic fluid includes incrementally increasing the injection pressure of the non-pharmacologic fluid until injection of the non-pharmacologic fluid simulates hyperemia across the lesion and wherein the step of measuring a distal pressure is performed continuously during continued administration of the non-pharmacologic fluid at the injection pressure sufficient to simulate hyperemia across the lesion.

12. A method of determining a pressure gradient across a lesion of a vessel, the method comprising the steps of:
percutaneously delivering a pressure-sensing instrument having at least a first pressure sensor at a distal portion thereof through a vasculature until the first pressure sensor is positioned adjacent to and distal to the lesion;
distally advancing a catheter over the pressure-sensing instrument via a first lumen of the catheter until a distal end of the catheter is positioned adjacent to and proximal to the lesion;
inflating a balloon at a distal portion of the catheter to block blood flow across the lesion;
injecting a non-pharmacologic fluid at an injection pressure through a second lumen of the catheter and across the lesion;
controlling the injection pressure to increase a flow rate across a portion of the vessel including the lesion;
measuring a distal pressure at a location distal to the lesion with the first pressure sensor of the pressure-sensing instrument, wherein the step of measuring a distal pressure occurs while the flow rate across the lesion is increased and until the measured distal pressure becomes constant thereby simulating hyperemia across the lesion;
measuring a proximal pressure at a location proximal to the lesion, wherein the steps of measuring distal and proximal pressures are performed while the portion of the vessel including the lesion has an increased flow rate there-through due to injection of the non-pharmacologic fluid; and
using the measured distal pressure when the measured distal pressure becomes constant and the measured proximal pressure to determine the pressure gradient across the lesion.

13. The method of claim 12, wherein the pressure-sensing instrument includes a second pressure sensor proximal to the first pressure sensor and the steps of measuring a distal pressure and measuring a proximal pressure are performed simultaneously, and wherein the step of measuring a proximal pressure is performed by the second pressure sensor of the pressure-sensing instrument.

14. The method of claim 12, wherein the pressure-sensing instrument includes only the first pressure sensor and the steps of measuring the distal pressure and measuring a proximal pressure are performed non-simultaneously, the proximal pressure being measured with the first pressure sensor of the pressure-sensing instrument.

15. The method of claim 12, wherein the non-pharmacologic fluid is blood or saline.

16. The method of claim 12, wherein the step of injecting a non-pharmacologic fluid includes gradually increasing the injection pressure of the non-pharmacologic fluid until injection of the non-pharmacologic fluid simulates hyperemia across the lesion and wherein the step of measuring a distal pressure is performed continuously during continued administration of the non-pharmacologic fluid at the injection pressure sufficient to simulate hyperemia across the lesion.

17. The method of claim 12, further comprising the step of:
using the pressure gradient to determine a fractional flow reserve (FFR) calculation.

* * * * *